(12) United States Patent
Boiteau et al.

(10) Patent No.: US 9,650,337 B2
(45) Date of Patent: May 16, 2017

(54) METHOD OF SYNTHESISING 4-PIPERIDIN-4-YL-BENZENE-1,3-DIOL AND THE SALTS OF SAME AND NOVEL COMPOUND TERT-BUTYL 4-(2,4-DIHYDROXY-PHENYL)-4-HYDROXY-PIPERIDINE-1-CARBOXYLATE

(71) Applicant: GALDERMA RESEARCH & DEVELOPMENT, Biot (FR)

(72) Inventors: Jean-Guy Boiteau, Valbonne (FR); Branislav Musicki, Nice (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 14/767,544

(22) PCT Filed: Feb. 14, 2014

(86) PCT No.: PCT/FR2014/050314
§ 371 (c)(1),
(2) Date: Aug. 12, 2015

(87) PCT Pub. No.: WO2014/125233
PCT Pub. Date: Aug. 21, 2014

(65) Prior Publication Data
US 2015/0376126 A1   Dec. 31, 2015

Related U.S. Application Data

(60) Provisional application No. 61/764,636, filed on Feb. 14, 2013.

(30) Foreign Application Priority Data

Feb. 14, 2013 (FR) .................................. 13 51253

(51) Int. Cl.
C07D 211/52 (2006.01)
C07D 211/22 (2006.01)
C07B 35/02 (2006.01)

(52) U.S. Cl.
CPC ............ *C07D 211/52* (2013.01); *C07B 35/02* (2013.01); *C07D 211/22* (2013.01)

(58) Field of Classification Search
CPC ............................. C07D 211/22; C07D 211/52
(Continued)

(56) References Cited

U.S. PATENT DOCUMENTS 4,147,872 A    4/1979  Althuis et al.
2011/0311466 A1*  12/2011  Boiteau ................ C07D 205/04
                                                              424/62

FOREIGN PATENT DOCUMENTS

WO   2004/010943 A2    2/2004
WO   2005/121087 A1   12/2005
(Continued)

OTHER PUBLICATIONS

Boiteau et al. "New 4-azacycloalkyl . . . " CA155:40809 (2011).*
(Continued)

*Primary Examiner* — Celia Chang
(74) *Attorney, Agent, or Firm* — Dentons US LLP

(57) ABSTRACT

A method is described for the synthesis of 4-piperidin-4-yl-benzene-1,3-diol of the following formula (I):
(Continued)

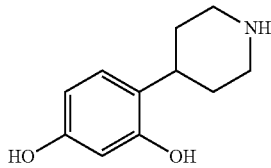

(I)

and the pharmaceutically acceptable salts thereof. Also described, is tert-butyl 4-(2,4-dihydroxy-phenyl)-4-hydroxy-piperidine-1-carboxylate as a novel intermediate compound

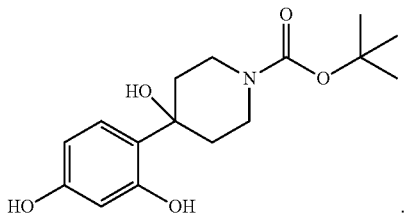

(10)

14 Claims, 2 Drawing Sheets

(58) Field of Classification Search
USPC .................................................. 546/217, 240
See application file for complete search history.

(56) References Cited

FOREIGN PATENT DOCUMENTS

| WO | 2007/092681 A2 | 8/2007 |
|---|---|---|
| WO | 2009/098576 A1 | 8/2009 |
| WO | 2010/063774 A1 | 6/2010 |
| WO | 2010/081904 A1 | 7/2010 |
| WO | 2011/033255 A1 | 3/2011 |
| WO | 2011/070080 A1 | 6/2011 |
| WO | WO2011070080 * | 6/2011 |
| WO | 2012/122391 A1 | 9/2012 |

OTHER PUBLICATIONS

Taber "functional group protection" Org. Chem. Portal p. 1-2 (2006).*
Boiteau et al. "New 4-(azacycloalkyl)benzene . . . " CA155:40809, CASreact (2011).*
International Search Report and Written Opinion dated Aug. 12, 2014 corresponding to International Patent Application No. PCT/FR2014/050314, 16 pages.
English Translation of the International Search Report dated Aug. 12, 2014 corresponding to International Patent Application No. PCT/FR2014/050314, 5 pages.
Pettersson, F., et al., "Synthesis and Evaluation of a Set of 4-Phenylpiperidines and 4-Phenylpiperazines as D2 Receptor Ligands and the Discovery of the Dopaminergic Stabilizer 4-[3-(Methylsulfony)pheyl]-1-propylpiperidine (Huntexil, Pridopidine, ACR16)," Journal of Medicinal Chemistry, vol. 53, No. 6, 2010, pp. 2510-2520.
Chiu, G., et al., "(Phenylpiperidinyl)cyclohexylsulfonamides: Development of .alpha.1a/1d-selective adrenergic receptor antagonists for the treatment of benign prostatic hyperplasia/lower urinary track symptoms (BPH/LUTS)," Bioorganic & Medicinal Chemistry Letters, vol. 17, No. 14, 2007, pp. 3930-3934.

* cited by examiner

METHOD OF SYNTHESISING 4-PIPERIDIN-4-YL-BENZENE-1,3-DIOL AND THE SALTS OF SAME AND NOVEL COMPOUND TERT-BUTYL 4-(2,4-DIHYDROXY-PHENYL)-4-HYDROXY-PIPERIDINE-1-CARBOXYLATE

CROSS-REFERENCE TO PRIOR APPLICATIONS

This application is a National Stage of PCT/FR2014/050314, filed Feb. 14, 2014, and designating the United States (published on Aug. 21, 2014, as WO 2014/125233 A1), which claims priority under 35 U.S.C. §119 to U.S. Provisional Patent Application No. 61/764,636, filed Feb. 14, 2014, and French Patent Application No. 1351253, filed Feb. 14, 2013, each hereby expressly incorporated by reference in its entirety and each assigned to the assignee hereof.

The present invention relates to a process for the synthesis of 4-piperidin-4-yl-benzene-1,3-diol of the following formula (I):

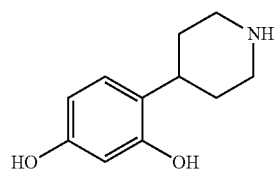

(I)

and pharmaceutically acceptable salts thereof.

The present invention also relates to the compound tert-butyl 4-(2,4-dihydroxy-phenyl)-4-hydroxy-piperidine-1-carboxylate of the formula (10)

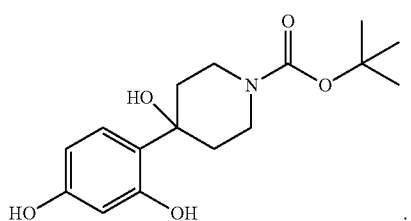

(10)

The synthesis of compounds similar to those of the compound (I) above and corresponding to the following general formula:

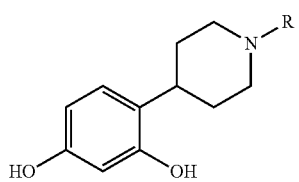

wherein R is a hydrogen atom or a —COR$^1$ radical was described in the patent application WO 2010/063774. Said synthesis is carried out in six steps (FIG. 1).

In the first step of said process (FIG. 1), the 2,4-dibenzyloxy bromobenzene (1) [X=Br; Y=H],

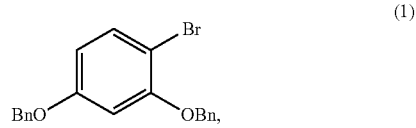 [SMILES: Brc1ccc(OCc2ccccc2)cc1OCc1ccccc1]

(1)

reacts in the presence of butyllithium with the azacycloalkanones of the general formula (2) to yield the corresponding benzylic alcohols of the general formula (3)

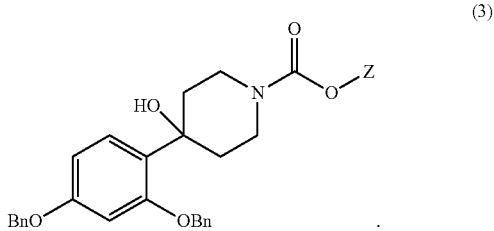

(3)

The alcohol functional group of the compound (3) is then removed by means of a reduction step, but these reducing conditions also cause deprotection of the phenol functional groups (removal of the benzyl protecting group) and give compound (4).

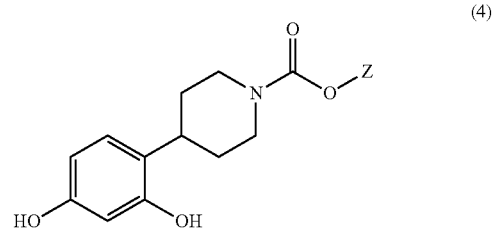

(4)

Said reduction step is a disadvantage in said synthesis, because the phenol functional groups of the compound (4) must be reprotected in the following step to yield the compound (5)

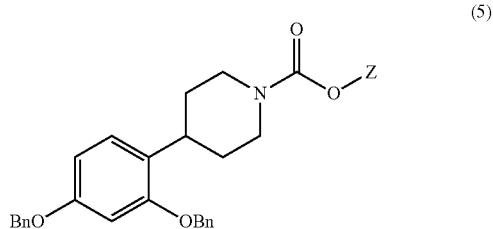

(5)

before being able to specifically eliminate the carbamate protecting group on the nitrogen of the compound (5) and to obtain the compound (6).

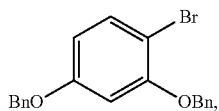

reacts in the presence of butyllithium with the azacycloalkanones of the general formula (2) to yield the corresponding benzylic alcohols of the general formula (3)

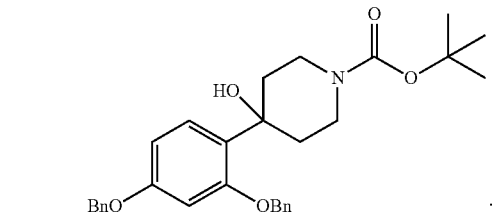

During the following step, the reducing conditions applied reduce the alcohol functional group and deprotect the phenol functional groups to yield the compound (4).

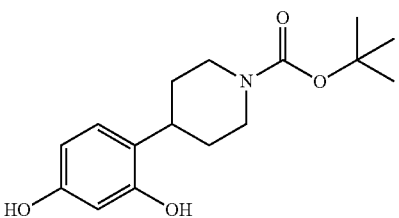

Said synthesis requires two more steps following compound (4) to yield the compounds of the formula (III)

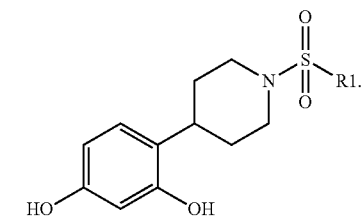

In the context of the development of the compounds of the formula (II) or (III), there is a need to have a simple and economical method for preparing in just a few steps and under safe conditions the 4-piperidin-4-yl-benzene-1,3-diol of the formula (I) while avoiding the disadvantages mentioned above.

The present invention thus aims to solve the problems cited above by proposing a process for the synthesis in two steps of the 4-piperidin-4-yl-benzene-1,3-diol of the formula (I) or salts thereof, easily adapted to an industrial scale.

The subject matter of the present invention relates to a process for the synthesis of the 4-piperidin-4-yl-benzene-1,3-diol corresponding to the general formula (I) and salts thereof

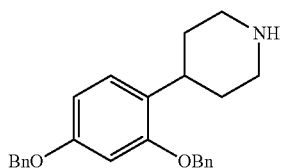

From said compound (6), an acyl (—COR$^1$) group is added on the nitrogen to yield the compound (7).

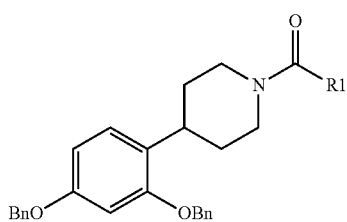

Lastly, a final deprotection step (debenzylation) of the phenol functional groups yields the compounds of the formula (II).

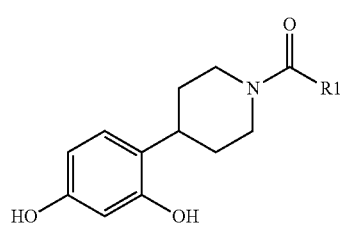

In total, said synthesis requires two steps of deprotection of the phenol functional groups (steps 2 and 6), one step of deprotection of the nitrogen functional group (step 4) and one step of protection of the phenol functional groups (step 3) to yield the compounds of the formula (I). Said succession of protection and deprotection steps thus constitutes a major disadvantage of the synthesis as described in the application WO 2010/063774, said disadvantage not allowing said synthesis to be adapted to an industrial scale.

The patent application WO 2011/070080 also describes a synthesis of compounds similar to the compound (I) above, compounds which correspond to the following general formula:

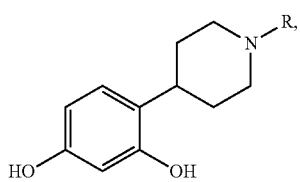

wherein R is a hydrogen atom or an —SO$_2$R$^1$ radical. Said synthesis is carried out in four steps (FIG. 2).

In the first step of the process as described in the patent application WO 2011/070080 (FIG. 2), the 2,4-dibenzyloxy bromobenzene (1) [X=Br; Y=H],

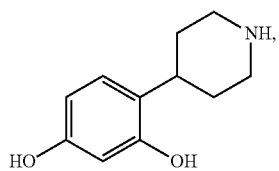

characterized in that the compound corresponding to the general formula (10)

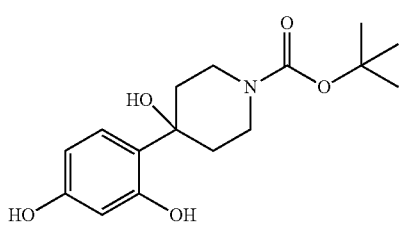

reacts first with hydrogen in the presence of a palladium-based catalyst in polar solvent and then with an inorganic or organic acid.

Preferably, the polar solvent is selected from the group comprising alcohols such as methanol, ethanol and isopropanol, for example, carboxylic acids such as acetic acid, for example, esters such as ethyl acetate, for example, ethers such as tetrahydrofuran, for example, water, and a mixture of said solvents. Advantageously, the polar solvent is an alcohol selected from methanol, ethanol and isopropanol.

Preferably, the palladium-based catalyst is selected from the group consisting of palladium on carbon, palladium hydroxide and palladium acetate.

Preferably, the hydrogen pressure applied in the process of the invention is between 1 bar and 10 bar.

In a particular embodiment, the compound corresponding to the general formula (10) is obtained by reacting the resorcinol with the azacycloalkone of the formula (9)

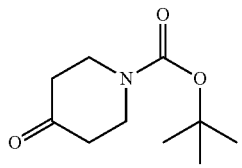

in the presence of a base and in polar solvent.

Preferably, the polar solvent is selected from the group comprising water and alcohols, preferably methanol, ethanol, isopropanol, n-butanol and tert-butanol.

Preferably, the base is selected from the group comprising sodium hydroxide, potassium hydroxide, lithium hydroxide, metal alcoholates, preferably sodium methanolate, sodium tert-butylate, potassium tert-butylate or lithium tert-butylate.

Preferably, the resorcinol and the azacycloalkanone (9) are used in a resorcinol/azacycloalkanone molar ratio between 1 and 8.

Another subject matter of the invention relates to the tert-butyl 4-(2,4-dihydroxy-phenyl)-4-hydroxy-piperidine-1-carboxylate of the formula (10)

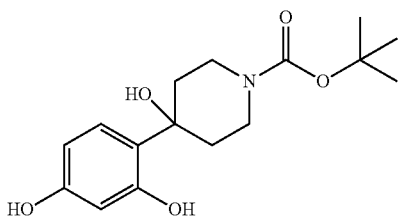

As illustrated in FIG. 3, the novel process for synthesis of the 4-piperidin-4-yl-benzene-1,3-diol (I), the subject matter of the present invention, is a short synthesis comprising two steps.

Said novel synthetic pathway uses the resorcinol (8) as the starting product, which is very advantageous economically compared with the price of the 2,4-dihydroxy bromobenzene (1) used in the syntheses described in applications WO 2010/063774 and WO 2011/070080.

The first step of said novel synthetic pathway is an original step of coupling the resorcinol (8) with the azacycloalkanone (9) in the presence of a base. The base used is selected preferably from the group comprising sodium hydroxide, potassium hydroxide, lithium hydroxide, and metal alcoholates such as sodium methanolate, sodium tert-butylate, potassium tert-butylate or lithium tert-butylate, for example. Said step is carried out in polar solvent, preferably in water or alcohols, or in a mixture of said solvents, and produces the compound (10) directly. The alcohols are selected preferably from the group comprising methanol, ethanol, isopropanol, n-butanol and tert-butanol.

During said first step, excess resorcinol (8) is preferably used to react on the azacycloalkanone (9). More specifically, the resorcinol (8)/azacycloalkanone (9) molar ratio is between 1 and 8, preferably between 2 and 4.

The temperature at which said coupling step is carried out is another advantage of said novel synthetic pathway. Indeed, said first step is carried out at room temperature, in water or alcohols, which avoids the cryogenic step (−78° C.) of the processes disclosed in WO 2010/063774 and WO 2011/070080. Furthermore, the reaction intermediate (10) of said first step is obtained in crystalline form, thus avoiding the need for purification steps. Thus, techniques for separation on a chromatography column to isolate the intermediate (10) are not necessary, which is another advantage for the adaptation of said process to an industrial scale.

The second step of said novel synthetic pathway is a hydrogenation reaction of the intermediate (10) to obtain the 4-piperidin-4-yl-benzene-1,3-diol (I).

The hydrogenation of the intermediate (10) is carried out in polar solvent. The preferred polar solvents are selected from the group comprising alcohols such as methanol, for example, carboxylic acids such as acetic acid, for example, esters such as ethyl acetate, for example, ethers such as tetrahydrofuran, for example, water, and a mixture of said solvents. The alcohols are selected preferably from the group comprising methanol, ethanol and isopropanol. Hydrogenation is carried out in the presence of a palladium-based catalyst. The preferred catalysts are selected from the group consisting of palladium on carbon, palladium hydroxide, palladium acetate, or any other reduction catalyst known to the skilled person. The hydrogen pressure applied is between 1 bar and 10 bar, preferably between 3 bar and 7 bar.

Said step has the advantage of producing the 4-piperidin-4-yl-benzene-1,3-diol (I) as a salt after the addition of an inorganic or organic acid to the reaction medium. The tert-butyl carbamate group protecting the nitrogen of the compound (10) is then cleaved in situ by the inorganic or organic acid to yield the 4-piperidin-4-yl-benzene-1,3-diol (I) as a salt.

The inorganic acids used to obtain a salt of the 4-piperidin-4-yl-benzene-1,3-diol (I) are selected from the group comprising hydrochloric acid and sulphuric acid, for example.

The organic acids used to obtain a salt of the 4-piperidin-4-yl-benzene-1,3-diol (I) are selected from the group comprising trifluoromethanesulphonic acid and trifluoroacetic acid.

Said process thus has the advantage of providing the 4-piperidin-4-yl-benzene-1,3-diol (I) or a salt thereof in at most two reaction steps and is, therefore, much easier to adapt to an industrial scale than the processes of the prior art.

EXAMPLES

Figure 1:
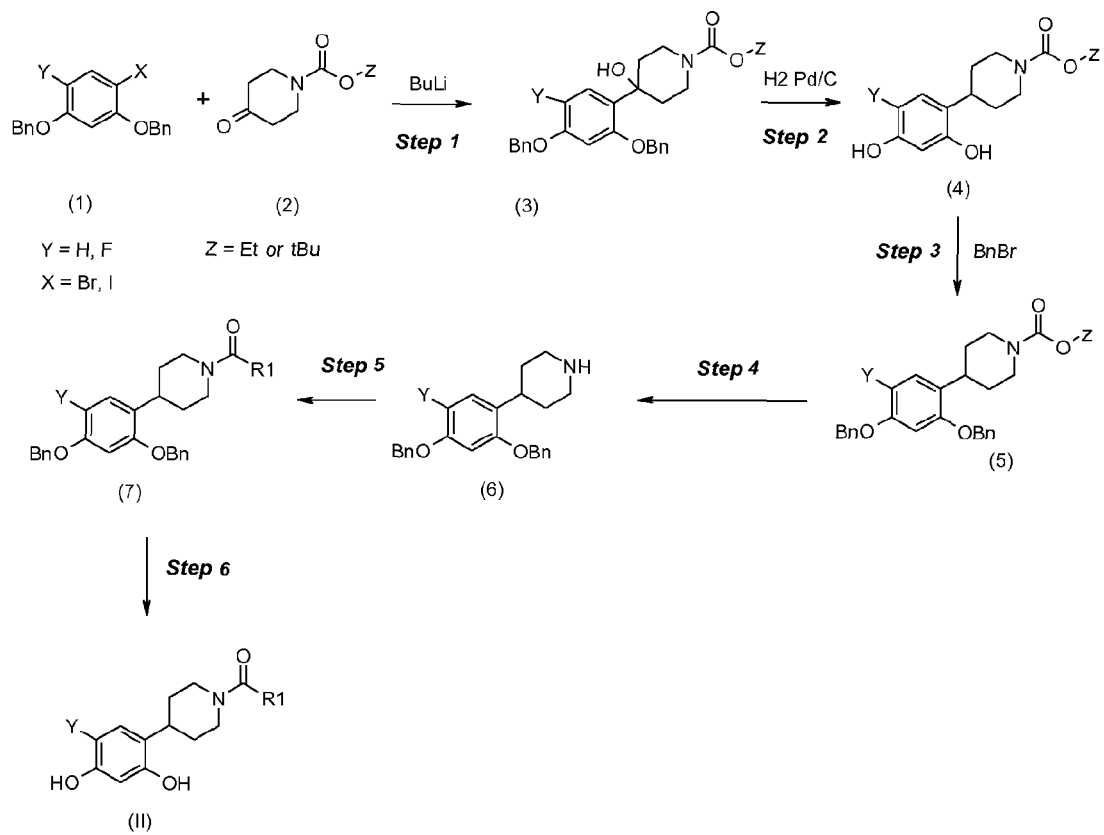
FIG. 1: Preparation of compounds of the formula (II) described in WO 2010/063774
Figure 2:
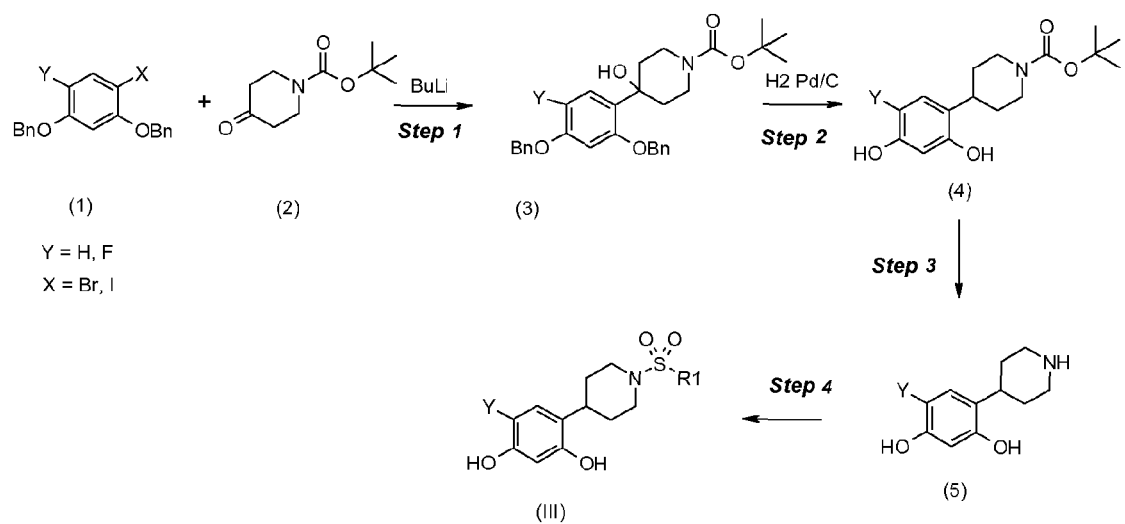
FIG. 2: Preparation of compounds of the formula (III) described in WO 2011/070080
Figure 3:
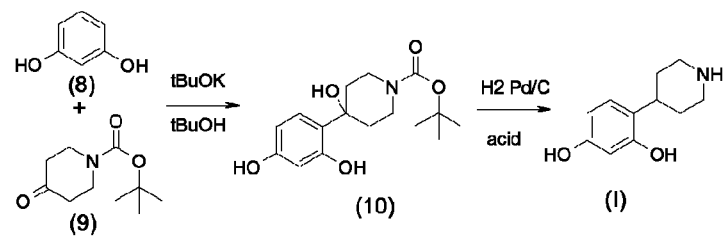
FIG. 3: Process for preparing the compounds of the invention of the formula (I) and salts thereof.

The following examples are now presented in order to illustrate the process as described above. Said examples which illustrate the process of the invention are not limiting.

Example 1

4-Piperidin-4-yl-benzene-1,3-diol hydrochloride

Step 1

4-(2,4-Dihydroxy-phenyl)-4-hydroxy-piperidine-1-carboxylic acid tert-butyl ester In a 4 liter reactor equipped with a mechanical stirrer and a thermometer, resorcinol (371.25 g) is placed in tert-butanol (2 L) at room temperature. To this heterogeneous mixture is then added potassium tert-butylate (378.0 g) over 5 min. The temperature increases to 55° C. and the reaction mixture becomes black. The reaction is stirred for 30 min allowing the mixture to cool to 38° C. Next, tert-butyl carboxylate (167.9 g) is added to the reaction mixture over 2 to 3 minutes. The addition is endothermic, lowering the temperature to 35° C. The reaction is then stirred for 1 hour until room temperature is reached. The reaction mixture is then added to a solution of NaH$_2$PO$_4$ (700 g) in water (5 l) and the aqueous phase is then extracted with 4 liters of an ethyl acetate/heptane (1:1) mixture. The organic phase is separated and washed with water (10×5 l). This operation is carried out until the resorcinol of the aqueous phase completely disappears (checked by TLC). The organic phase is then dried over Na$_2$SO$_4$ and the solvents are evaporated to yield 263 g of residue. The residue is dissolved in a minimum of dichloromethane and filtered on a silica gel patch using an ethyl acetate/heptane (1:1) mixture. After evaporation of the solvent (concentration), a solid begins to crystallise slowly. After 30 minutes, 117 g of tert-butyl 4-(2,4-dihydroxy-phenyl)-4-hydroxy-piperidine-1-carboxylate is obtained.

(Yield=45%).

$^1$H NMR (DMSO D6, 400 MHz): 1.40 (s, 9H); 1.52 (d, J=12.8 Hz, 2H); 2.10 (m, 1H); 3.08 (br s, 2H); 3.79 (br s, 2H); 5.35 (br s, 1H); 6.17 (dd, J=2.4 Hz, 8.3 Hz, 1H); 6.21 (d, J=2.4 Hz, 1H); 7.08 (d, J=8.2 Hz, 1H); 9.09 (br s, 1H); 9.47 (br s, 1H).

Step 2

4-Piperidin-4-yl-benzene-1,3-diol hydrochloride

In a 1 liter hydrogenation reactor, 70 g of tert-butyl 4-(2,4-dihydroxy-phenyl)-4-hydroxy-piperidine-1-carboxylate (0.226 mol) is dissolved in 500 ml of glacial acetic acid with 4 g of 10% palladium on carbon (Pd/C) and the mixture is hydrogenated at 5 bar and 35° C. for 3 hours. During hydrogenation, the temperature increases to 65° C. After 3 hours, 500 ml of ethyl acetate is added to the reaction mixture and the solution is filtered on Celite. On said filtrate, 150 ml of a 4 M solution of HCl dissolved in ethyl acetate is then added dropwise and after 2 hours of stirring the precipitate formed is filtered, yielding 36 g of 4-piperidin-4-yl-benzene-1,3-diol hydrochloride as white crystals.

Yield=69%

$^1$H NMR (DMSO D6, 400 MHz): 1.80 (m, 4H); 2.92 (m, 3H); 3.28 (d, J=12 Hz, 2H); 6.18 (dd, J=2.4 Hz, 8.3 Hz, 1H); 6.34 (d, J=2.4 Hz, 1H); 6.77 (d, J=8.2 Hz, 1H); 8.93 (br s, 1H); 9.10 (br s, 1H); 9.36 (s, 1H).

$^{13}$C NMR (DMSO D6, 100 MHz): 28.3; 32.4; 43.8; 102.5; 106.1; 121.1; 126.5; 155.3; 156.5.

The invention claimed is:

1. A method of synthesizing 4-piperidin-4-yl-benzene-1,3-diol corresponding to general formula (I) and salts thereof

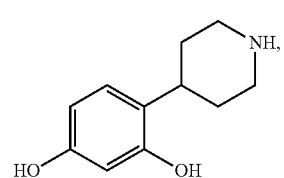

(I)

the method comprising:

(1) reacting resorcinol with azacycloalkanone of formula (9)

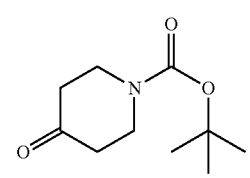

(9)

in the presence of a base and in a polar solvent to obtain a compound corresponding to general formula (10)

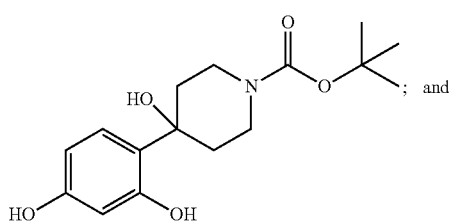

(2) reacting the compound corresponding to general formula (10) obtained in step (1) with hydrogen in the presence of a palladium-based catalyst in polar solvent and then reacting the obtained product with an inorganic or organic acid.

2. The method according to claim 1, wherein the polar solvent is selected from the group consisting of alcohols, carboxylic acids, esters, ethers, water, and a mixture thereof.

3. The method according to claim 2, wherein the alcohols are selected from the group consisting of methanol, ethanol and isopropanol.

4. The method according to claim 1, wherein the polar solvent is selected from the group consisting of water and alcohols.

5. The method according to claim 1, wherein the base is selected from the group consisting of sodium hydroxide, potassium hydroxide, lithium hydroxide, and metal alcoholates.

6. The method according to claim 1, wherein the palladium-based catalyst is selected from the group consisting of palladium on carbon, palladium hydroxide and palladium acetate.

7. The method according to claim 1, wherein the hydrogen pressure applied is from 1 bar to 10 bar.

8. The method according to claim 1, wherein the resorcinol and the azacycloalkanone (9) are used in a resorcinol/azacycloalkanone molar ratio from 1 to 8.

9. The method according to claim 2, wherein when the solvent is an alcohol, the alcohol is methanol.

10. The method according to claim 2, wherein when the solvent is a carboxylic acid, the carboxylic acid is acetic acid.

11. The method according to claim 2, wherein when the solvent is an ester, the ester is ethyl acetate.

12. The method according to claim 2, wherein when the solvent is an ether, the ether is tetrahydrofuran.

13. The method according to claim 4, wherein when the polar solvent is an alcohol, it is selected from the group consisting of methanol, ethanol, isopropanol, n-butanol, and tert-butanol.

14. The method according to claim 5, wherein when the base is selected from the group consisting of sodium methanolate, sodium tert-butylate, potassium tert-butylate and lithium tert-butylate.

* * * * *